United States Patent [19]

Altorfer et al.

[11] 4,189,576

[45] Feb. 19, 1980

[54] PROCESS FOR MONOACYLATING WATER-SOLUBLE ORGANIC AMINO COMPOUNDS

[75] Inventors: Fritz Altorfer, Basel; Sandor Gati, Birsfelden; Gert Hegar, Schönenbuch, all of Switzerland

[73] Assignee: Ciba-Geigy Corporation, Ardsley, N.Y.

[21] Appl. No.: 841,865

[22] Filed: Oct. 13, 1977

[30] Foreign Application Priority Data

Oct. 15, 1976 [CH] Switzerland ................ 13092/76

[51] Int. Cl.$^2$ ........................................... C07D 251/44
[52] U.S. Cl. .................................................. 544/211
[58] Field of Search ................ 544/211; 260/146 T, 260/153

[56] References Cited

U.S. PATENT DOCUMENTS 3,945,989  3/1976  Angliker et al. ................ 544/211

FOREIGN PATENT DOCUMENTS 1644208  9/1970  Fed. Rep. of Germany.
1188606  4/1970  United Kingdom.

*Primary Examiner*—John M. Ford
*Attorney, Agent, or Firm*—Prabodh I. Almaula

[57] ABSTRACT

A process for the monoacylation of water-soluble organic amino compounds with 2,4,6-trifluoro-s-triazine, which comprises introducing all reactants simultaneously and continuously in the amounts necessary for the required throughput into the reaction space and removing the resultant reaction products continuously therefrom.

8 Claims, No Drawings

PROCESS FOR MONOACYLATING WATER-SOLUBLE ORGANIC AMINO COMPOUNDS

The monoacylation of water-soluble organic amino compounds with 2,4,6-trifluoro-s-triazine (cyanuric fluoride) by the conventional process, the semi-continuous reaction method, i.e. in such a manner that cyanuric fluoride is added at a specific rate to an amino compound dissolved in aqueous solution, frequently proceeds inhomogeneously, since on account of the high reactivity of the primary monocondensation products of cyanuric fluoride, these immediately react further with non-acylated amino compound still present to give dicondensation products. Especially water-soluble organic amino compounds, which react with cyanuric fluoride smoothly and rapidly, cannot therefore be condensed homogeneously with cyanuric fluoride. Such rapidly reacting amino compounds which yield primarily dicondensation products during the reaction with cyanuric fluoride by the conventional process are for example metanilic acid, sulphanilic acid, 1,3-phenylenediamine-4-sulphonic acid, 1,4-phenylenediamine-2-sulphonic acid and 1,4-phenylenediamine-2,5-disulphonic acid.

It has now been found that the disadvantage of the formation of dicondensation products can be avoided by carrying out the reaction between cyanuric fluoride and amino compound continuously.

The process of the present invention for monoacylating water-soluble organic amino compounds with 2,4,6-trifluoro-s-triazine comprises introducing all reactants in the amounts required for the desired throughput simultaneously and continuously into the reaction space and removing the resultant reaction products therefrom continuously.

The reactions are carried out in suitable reaction vessels which permit the reactants to be introduced simultaneously and continuously and the resultant reaction products to be drawn off again continuously when the reaction is complete.

A reactor suitable for carrying out the reaction of the present invention is described in the literature (see e.g. Ullmanns Encyklopädie der technischen Chemie, Verlag Chemie, Weinheim/Bergstr., 4th edition (1973), vol. 3, page 345 ff.; D. Fitzer and W. Fritz, Technische Chemie, Springer-Verlag, Berlin/Heidelberg/New York, 1975, page 264 ff.). This reactor is the "Idealkessel" with continuous flow and complete backmixing of the reaction mass in the reactor. The sojourn time of the reactants necessary for the desired reaction course in the reaction space is dependent on the mutual reactivity of the reactants and can be determined by means of simple preliminary trials.

The foregoing description makes it evident that, in comparison to the conventional method, the process of the present invention has, aside from the chemical advantage (avoidance of the formation of dicondensation product and thus increase in yield), also a technical advantage from the point of view of the apparatus used, which consists in only small reaction vessels being required, especially at high reaction rates.

The monocondensation products of water-soluble organic amino compounds with 2,4,6-trifluoro-s-triazine are useful intermediates which are suitable in particular for the manufacture of fibre-reactive dyes. For this purpose, the 2-amino-substituted 4,6-difluoro-s-triazines obtained by the process of the present invention are condensed in the molar ratio 1:1 with dyes (or optionally dye primary products) which contain an acylatable amino group, so that an additional removable fluorine atom remains at the s-triazine ring.

Particularly important 2-amino-substituted 4,6-difluoro-s-triazines which can be obtained by the process of the present invention and are suitable intermediates for the manufacture of fibre-reactive dyes, are 2-arylamino-4,6-difluoro-s-triazines which can contain further substituents in the aryl radical (for example a benzene or naphthalene radical), such as low molecular alkyl and alkoxy groups, halogen atoms, amino groups, carboxyl groups and in particular sulpho groups. The following compounds may be cited as examples of water-soluble organic amino compounds which can be monoacylated with 2,4,6-trifluoro-s-triazine by the process of the present invention:

1-aminobenzene-2-sulphonic acid,
1-aminobenzene-3-sulphonic acid,
1-aminobenzene-4-sulphonic acid,
1-amino-4-methylbenzene-3-sulphonic acid,
1-amino-4-methoxybenzene-3-sulphonic acid,
1-amino-2-methylbenzene-4-sulphonic acid,
1-amino-3-methylbenzene-4-sulphonic acid,
1-aminobenzene-3,5-disulphonic acid,
4-aminobenzoic acid,
2-amino-5-sulphobenzoic acid,
1-aminonaphthalene-4-sulphonic acid,
1-aminonaphthalene-5-sulphonic acid,
1-aminonaphthalene-6-sulphonic acid,
2-aminonaphthalene-5-sulphonic acid,
2-aminonaphthalene-7-sulphonic acid,
2-aminonaphthalene-4,8-disulphonic acid,
2-aminonaphthalene-5,7-disulphonic acid,
2-aminoethanesulphonic acid,
1,4-diaminobenzene-2,5-disulphonic acid,
1,3-diaminobenzene-4-sulphonic acid,
1,4-diaminobenzene-2-sulphonic acid,
1,3-diaminobenzene-4,6-disulphonic acid.

In a further preferred embodiment of the process of the present invention, chromophoric water-soluble organic compounds which contain acylatable amino groups are monoacylated with 2,4,6-trifluoro-s-triazine. As water-soluble organic amino compounds with chromophoric character it is possible to use in particular the amino group-containing dyes and dye intermediates known from the chemistry of reactive dyes. In the difluoro-s-triazine dyes obtained in this manner a fluorine atom at the s-triazine ring can be replaced by the corresponding amino group by subsequent condensation with a colourless amino compound, for example 1-amino-2-methylbenzene, 1-aminobenzene-3-sulphonic acid etc., in the molar ratio 1:1.

The first Example and also the subsequently described comparison experiment show that the reaction of metanilic acid with cyanuric fluoride by the conventional method yields primarily 2-fluoro-4,6-bis-3'-sulphophenylamino-s-triazine, whilst the monocondensation product, 2-(3'-sulphophenylamino)-4,6-difluoro-s-triazine, is obtained in high yield by the process of the invention.

The invention is illustrated by the following Examples in which the parts and percentages are by weight unless otherwise indicated.

EXAMPLE 1

2-(3'-Sulphophenylamino)-4,6-difluoro-1,3,5-triazine 0.1 mole per minute of the sodium salt of 1-aminobenzene-3-sulphonic acid (as 4% aqueous solution) and 8.7 parts by volume per minute of 2,4,6-trifluoro-1,3,5-triazine are introduced continuously into the bottom part of a cylindrical reaction vessel which is provided with a cooling jacket, while the pH value in the reaction space is kept at 6.5 by the simultaneous addition of 30% sodium hydroxide solution. Cooling brine circulates in the cooling jacket of the reaction vessel in order to keep the temperature between 0° and 5° C. during the reaction. The sojourn time in the reaction vessel is about one minute. The overflowing reaction mixture is collected in a storage vessel. No more aminobenzenesulphonic acid can be detected in the reaction mixture and the content of by-products is less than 2%. In analogous manner, further 2-arylamino-4,6-difluoro-1,3,5-triazines are obtained in good yield by reacting the following water-soluble arylamines instead of 1-aminobenzene-3-sulphonic acid with 2,4,6-trifluoro-1,3,5-triazine in accordance with the particulars of this Example:

1-aminobenzene-4-sulphonic acid,
1-amino-4-methylbenzene-3-sulphonic acid,
1-amino-4-methoxybenzene-3-sulphonic acid,
1-amino-2-methylbenzene-4-sulphonic acid,
1-amino-3-methylbenzene-4-sulphonic acid,
1-aminobenzene-3,5-disulphonic acid,
4-aminobenzoic acid,
2-amino-5-sulphobenzoic acid,
1-aminonaphthalene-4-sulphonic acid,
1-aminonaphthalene-5-sulphonic acid,
1-aminonaphthalene-6-sulphonic acid,
2-aminonaphthalene-5-sulphonic acid,
2-aminonaphthalene-7-sulphonic acid,
2-aminonaphthalene-4,8-disulphonic acid,
2-aminonaphthalene-5,7-disulphonic acid,
2-aminoethanesulphonic acid.

COMPARISON EXAMPLE 17.3 g of 1-aminobenzene-3-sulphonic acid are suspended in 300 ml of water, dissolved by addition of 2 N sodium hydroxide solution at pH 6.5 and the solution is adjusted to a volume of 490 ml. A 4% solution of the sodium salt of 1-aminobenzene-3-sulphonic acid is obtained. This solution is cooled to 0° C. and in the course of 1 minute 8.7 ml of 2,4,6-trifluoro-1,3,5-triazine are added. The pH value of the solution is kept at 6.5 by simultaneous addition of 30% sodium hydroxide solution. When the addition of the trifluorotriazine is complete, no more aminobenzenesulphonic acid can be detected. The analysis of the reaction mixture shows that only about 30% of the desired monocondensation product has been obtained, whilst the remainder consists of 2,4-bis-(3'-sulphophenylamino)-6-fluoro-1,3,5-triazine and hydrolysis products of 2,4,6-trifluoro-1,3,5-triazine.

EXAMPLE 2

59.5 parts of the copper complex of 3''-amino-2'-carboxy-2''-hydroxy-4',5''-disulpho-1,3,5-triphenylformazane are suspended in 150 parts of water and the mixture is adjusted to a pH of 7.5. Then 520 parts by volume of an aqueous solution according to Example 1 containing 31 parts of the sodium salt of 2-(3'-sulphophenylamino)-4,6-difluoro-1,3,5-triazine are poured into the above mixture. The hydrogen fluoride set free during the condensation is neutralised continuously by the dropwise addition of 2 N sodium hydroxide solution. The condensation is complete when no more sodium hydroxide is consumed. In a chromatogram a sample shows no more starting dye. Sodium chloride is added to the blue reaction mixture and the precipitated dye is collected by suction filtration and dried. It dyes cotton from an aqueous bath in fast blue shades.

EXAMPLE 3

An aqueous solution containing 0.2 mole/liter of the sodium salt of 1-aminobenzene-2-sulphonic acid and 0.05 mole/liter of disodium hydrogen phosphate is introduced at an initial temperature of 21° C. continuously into the reactor described in Example 1. With very rapid mixing of the reactor contents, 2,4,6-trifluoro-1,3,5-triazine is introduced simultaneously and continuously into the reaction space, while keeping the pH of the reaction mixture at 7 by the addition of 30% sodium hydroxide solution. The throughput of both reactants is 0.075 mole/min. and the sojourn time in the reactor is approx. 3 minutes. The reaction mixture, which is collected in a storage vessel, contains as main product 2-(2'-sulphophenylamino)-4,6-difluoro-1,3,5-triazine. 6.8% of the starting 1-aminobenzene-2-sulphonic acid remains unreacted (titration). Thin-layer chromatography shows that the reaction mixture contains no 2,4-bis-(2'-sulphophenylamino)-6-fluoro-1,3,5-triazine. Reaction of 480 parts of the above monocondensate with 48 parts of the copper complex of 3''-amino-2'-carboxy-2''-hydroxy-4',5''-disulpho-1,3,5-triphenylformazane (in the same manner as described in Example 2) affords, after isolation of the reaction product, a reactive dye which dyes cotton from an aqueous bath in fast blue shades.

EXAMPLE 4

A 0.0825 molar neutral aqueous solution of the sodium salt of 2-(2'-ureido-4'-amino-azophenyl)-naphthalene-3,6,8-trisulphonic acid, containing 0.035 mole/liter of disodium hydrogen phosphate, is passed at an initial temperature of 10° C. through the reactor described in Example 1 at a throughput of 0.03375 mole/min. Then 2,4,6-trifluoro-1,3,5-triazine is introduced into the reaction space simultaneously and continuously at a throughput of 0.0375 mole/min., while keeping the pH at 7 by the addition of 30% sodium hydroxide solution. The sojourn time of the reaction mixture in the reactor is approx. 2 minutes. The temperature of the reaction solution issuing from the reactor is kept at 11° C. by cooling brine which circulates in the double jacket of the reactor.

In addition to 13% unreacted monoazo dye, the reaction solution contains 2-[2'-(2''-ureido-4''-aminoazopheny)-3',6',8'-trisulphonaphthyl]-4,6-difluoro-1,3,5-triazine as main product. No bicondensate can be detected in a thin-layer chromatogram. Reaction of 1260 parts of the monocondensate solution with 11 parts of 2-methyl-aniline and neutralisation of the hydrofluoric acid which forms during the reaction with concentrated sodium hydroxide solution while warming the reaction solution to 30° C., yields a reactive dye which can be isolated when the reaction is complete by adding sodium chloride to the reaction solution and which dyes cotton in the presence of alkalies from an aqueous bath in fast reddish yellow shades.

EXAMPLE 5

By substituting for the aqueous solution of 2-(2'-ureido-4'-amino-azophenyl)-naphthalene-3,6,8-trisulphonic acid used in Example 4 an aqueous solution of 4-(2'-sulpho-5'-aminophenylazo)-1-(4'',8''-disulphonaphth-2''-yl)-3-methyl-pyrazol-5-one and condensing this solution in the continuous procedure with 2,4,6-trifluoro-1,3,5-triazine in accordance with the particulars of Example 4, a monocondensate solution is obtained in which no bicondensate can be determined by thin-layer chromatography.

Further reaction of the monocondensate solution with 2-methylaniline in accordance with the particulars of Example 4 yields a reactive dye which can be isolated from the reaction solution and which dyes cotton in the presence of alkalies from an aqueous bath in fast greenish yellow shades.

EXAMPLE 6

A 0.22 molar neutral aqueous solution of the disodium salt of 1,4-phenylenediamine-2,5-disulphonic acid, containing 0.044 mole/liter of disodium hydrogen phosphate, is passed at an initial temperature of −1° C. continuously through the reactor described in Example 1. With very rapid stirring, 2,4,6-trifluoro-1,3,5-triazine is introduced simultaneously and continuously into the reaction space, while keeping the pH at 7 by the addition of 30% sodium hydroxide solution. The throughput of both reactants is 0.1 mole/min. and the temperature of the condensate issuing from the reactor is 3° C. (brine cooling through the double jacket of the reactor). The solution collected in a storage vessel contains as main product 2-(4'-amino-2',5'-disulphophenylamino)-4,6-difluoro-1,3,5-triazine and only traces of 2,4-bis-(4'-amino-2',5'-disulphophenylamino)-4-fluoro-1,3,5-triazine. Then 950 parts of the resultant monocondensate solution are rapidly treated with a solution of 34.6 parts of aniline-3-sulphonic acid in 150 parts of water. The acid which is set free is continuously neutralised with 30% sodium hydroxide solution. When the addition of sodium hydroxide is complete, the solution of the bicondensate is diazotised at 0° C. to 5° C. with hydrochloric acid and sodium nitrite by the conventional method and a neutral solution of 54 parts of 1-ethyl-2-hydroxy-4-methyl-5-sulphomethyl-pyrid-6-one-3-carboxamide is added to the diazo solution after excess nitrous acid has been destroyed. The acid set free during the coupling is continuously neutralised by introducing 30% sodium hydroxide solution at pH 7.5. After the diazo component has been consumed, the dye solution is salted out with 164 parts of potassium chloride and the dye is isolated by filtration. The dye colours cellulosic materials from an aqueous bath in the presence of alkalies in fast greenish yellow shades.

Homogeneous monoacylation products in high yields are also obtained by the above process by using instead of 1,4-diaminobenzene-2,5-disulphonic acid:
1,3-diaminobenzene-4-sulphonic acid,
1,4-diaminobenzene-2-sulphonic acid or
1,3-diaminobenzene-4,6-disulphonic acid.

What is claimed is:

1. A process for the monoacylation of water-soluble aminoaryl sulfonic or carboxylic acid, with 2,4,6-trifluoro-s-triazine, which comprises introducing all reactants simultaneously and continuously in the amounts necessary for the required throughput into the reaction space and removing the resultant reaction products continuously therefrom.

2. A process according to claim 1 wherein the water-soluble organic amino compound is an aminonaphthalenesulphonic acid.

3. A process of claim 1, wherein the aminoaryl sulfonic or carboxylic acid is a compound of the formula $$H_2N-\underset{X}{\underset{|}{\bigcirc}}\overset{Z}{\underset{}{\underset{|}{-}}}Y$$

wherein X is hydrogen, methyl, amino or sulfo, Y is hydrogen, methyl, methoxy, amino, carboxy or sulfo and Z is hydrogen or sulfo.

4. A process of claim 3, wherein X is hydrogen, methyl or amino, Y is sulfo and Z is hydrogen.

5. A process of claim 3, wherein X is sulfo, Y is hydrogen, methyl, methoxy or amino and Z is hydrogen.

6. A process of claim 3, wherein X is sulfo, Y is hydrogen and Z is sulfo.

7. A process of claim 3, wherein X is hydrogen, Y is carboxy and Z is hydrogen.

8. A process according to claim 3 wherein 2,4,6-trifluoro-s-triazine and 1-aminobenzene-3-sulphonic acid are reacted with each other in the manner indicated in claim 3.

* * * * *

UNITED STATES PATENT AND TRADEMARK OFFICE
CERTIFICATE OF CORRECTION

PATENT NO. : 4,189,576
DATED : February 19, 1980
INVENTOR(S) : Fritz Altorfer et al.

It is certified that error appears in the above-identified patent and that said Letters Patent are hereby corrected as shown below:

Title page, [73] Assignee:

"Ciba-Geigy Corporation, Ardsley, N.Y."

should be

--Ciba-Geigy AG, Basle, Switzerland--.

Signed and Sealed this

Twenty-ninth Day of July 1980

[SEAL]

Attest:

SIDNEY A. DIAMOND

Attesting Officer

Commissioner of Patents and Trademarks